US008679999B2

(12) United States Patent
Kanagasabapathy et al.

(10) Patent No.: US 8,679,999 B2
(45) Date of Patent: Mar. 25, 2014

(54) PROCESS FOR REGENERATION OF TITANO SILICATE CATALYST

(71) Applicant: Aditya Birla Science and Technology Co. Ltd., Mumbai (IN)

(72) Inventors: Subbareddy Kanagasabapathy, Mumbai (IN); Yogesh Laxman Borle, Jalgaon (IN); Bir Kapoor, Mumbai (IN); Arati Verma, Mumbai (IN)

(73) Assignee: Aditya Birla Science & Technology Co. Ltd., Mumbai (IN)

(*) Notice: Subject to any disclaimer, the term of this patent is extended or adjusted under 35 U.S.C. 154(b) by 0 days.

(21) Appl. No.: 13/755,689

(22) Filed: Jan. 31, 2013

(65) Prior Publication Data

US 2013/0144075 A1 Jun. 6, 2013

Related U.S. Application Data

(63) Continuation of application No. PCT/IN2011/000512, filed on Aug. 3, 2011.

(30) Foreign Application Priority Data

Aug. 3, 2010 (IN) .......................... 2202/MUM/2010

(51) Int. Cl.
*B01J 38/52* (2006.01)
*B01J 38/04* (2006.01)
*C07D 301/12* (2006.01)
*C07C 45/00* (2006.01)

(52) U.S. Cl.
USPC ................ 502/33; 502/34; 549/531; 568/362

(58) Field of Classification Search
USPC ......................... 502/33, 34; 549/531; 568/362
See application file for complete search history.

(56) References Cited

U.S. PATENT DOCUMENTS

| 6,063,941 A | 5/2000 | Gilbeau |
| 6,169,050 B1 | 1/2001 | Catinat et al. |
| 6,288,248 B1 | 9/2001 | Strebelle et al. |
| 6,790,969 B2 | 9/2004 | Muller et al. |
| 6,958,304 B2 | 10/2005 | Teles et al. |
| 7,629,287 B2 | 12/2009 | Siler et al. |

FOREIGN PATENT DOCUMENTS

CN 101439301 5/2009

(Continued)

OTHER PUBLICATIONS

Liu, Hong et al. "Deactivation and regeneration of TS-1/diatomite catalyst for hydroxylation of phenol in fixed-bed reactor." Chemical Engineering Journal. vol. 108 2005. pp. 187-192.

Liu; Xuewu et al "Regeneration of lamina TS-1 catalyst in the epoxidetion of propylene with hydrogen peroxide." Catalysis Letters. vol. 97, Nos. 3-4. Sep. 2004, pp. 223-229.

(Continued)

*Primary Examiner* — Taylor Victor Oh
(74) *Attorney, Agent, or Firm* — Whiteford, Taylor & Preston, LLP; Joseph L. Morales

(57) ABSTRACT

Titanosilicate catalyst is used in the oxidation reactions such as allylchloride epoxidation, phenol hydroxylation, Cyclohexanone ammoximation. During the reaction the catalyst is deactivated which further decrease in the efficiency of the oxidation reactions. The present invention provides a method for an efficient regeneration of catalyst titanosilicate catalyst at low temperature below 100° C. using a gaseous mixture containing ozone, without isolating the catalyst from the reactor system.

14 Claims, 1 Drawing Sheet

(56) References Cited

FOREIGN PATENT DOCUMENTS

| | | |
|---|---|---|
| CN | 101455980 | 6/2009 |
| DE | 19528220 | 9/1997 |
| EP | 1283747 | 10/2004 |
| WO | 98/18555 | 5/1998 |
| WO | 98/18556 | 5/1998 |
| WO | 98/55228 | 12/1998 |
| WO | 01/41926 | 6/2001 |
| WO | 2005/000827 | 1/2005 |

OTHER PUBLICATIONS

Timofeeva, M.N. et al. "Titanium and cerium-containing mesoporous silicate materials as catalysts for oxidative cleavage of cyclohexene with H2O2: A comparative study of catalytic activity and stability." Applied Catalysis A: General. vol. 345. 2008. pp. 195-200.

Wang, Qingfa et al. "Deactivation and regeneration of titanium silicalite catalyst for epoxidation of propylene." Journal of Molecular Catalysis A: Chemical. vol. 273. 2007. pp. 73-80.

Zhang, Xiangjing et al. "Coke deposition and characterization on titanium silicate-1 catalyst in cyclohexanone ammoximation." Applied Catalysis A: General. vol. 307. 2006. pp. 222-230.

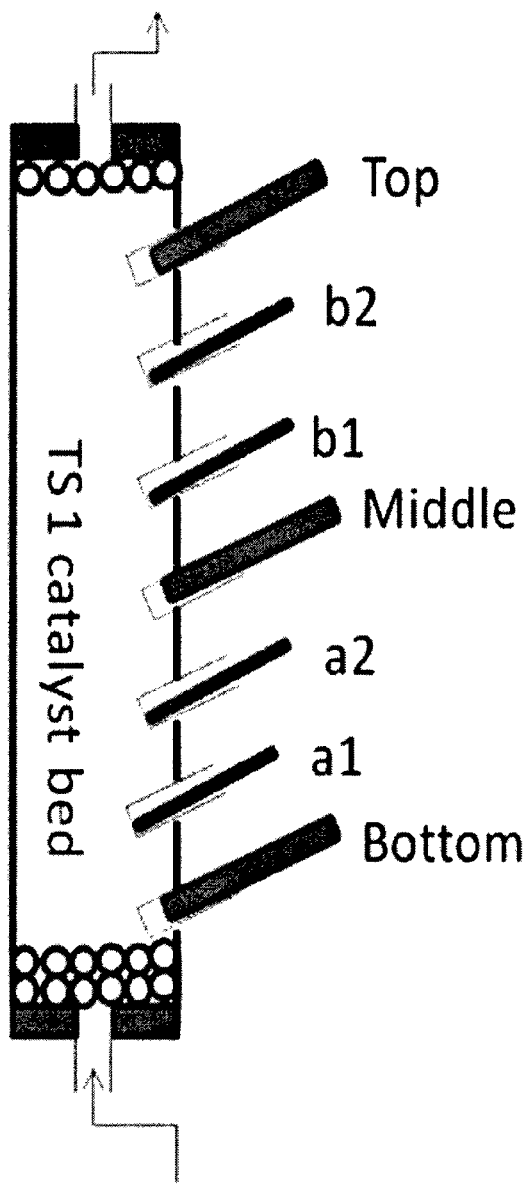

PROCESS FOR REGENERATION OF TITANO SILICATE CATALYST

CROSS REFERENCE TO RELATED APPLICATIONS

This application is a continuation of International Application No. PCT/IN2011/000512, filed Aug. 3, 2011, which claims priority to Indian Patent Application No. 2202/MUM/2010, filed Aug. 3, 2010.

FIELD OF THE INVENTION

The present invention relates to a process for regeneration of titanosilicate catalysts employed in oxidation reactions such as olefin epoxidation, phenol hydroxylation and cyclohexene ammoximation.

BACKGROUND

In recent times, olefin epoxidation with hydrogen peroxide has gained importance commercially. Epichlorohydrin is produced by olefin oxidation process of allylchloride with hydrogen peroxide in presence of a catalyst. The catalyst often employed is a titanium silicate catalyst. However, a serious problem associated with this process is that, the activity of the Titano Silicate catalyst is rapidly reduced due to deposition of organics on the catalyst.

Similar deactivation of the Titano Silicate catalyst is observed during propylene epoxidation, phenol hydroxylation and cyclohexene ammoximation processes. Thus, it is essential to have a means for regenerating the catalyst in order to use it repeatedly. Various methods/techniques to regenerate the epoxidation catalysts have been attempted.

PRIOR ART

U.S. Pat. No. 6,063,941, DE-A 19528220 and PCT publication no. 98/18555 disclose a process for the regeneration of titanosilicate catalysts in which the regeneration is carried out with a treatment of oxidizing agent such as hydrogen peroxide, organic peroxides or ozone in a liquid phase at pH range of 4-7. However, it has been observed that the regeneration of the catalyst is temporary and the catalyst loses its regained activity very rapidly.

PCT WO9855228, U.S. Pat. No. 6,169,050 and WO98018556 disclose a process in which the deactivated catalyst is first washed with solvents, removed from the reactor system and then regenerated by thermal treatment in presence of gaseous stream that includes one or more components chosen from nitrogen, oxygen and water. However, the process involves repeated removal of the catalyst from the reactor for such regeneration, thus making the overall process cycle laborious, time consuming and expensive in terms of catalyst losses.

U.S. Pat. No. 6,790,969 and U.S. Pat. No. 6,958,304 disclose a method for regeneration of a titano silicate catalyst used for propylene epoxidation. In this process, the catalyst regeneration is achieved through steps such as washing with a suitable solvent, drying the catalyst in the temperature range of 50 to 250° C., heating the catalyst further to a temperature of 450-600° C., and regenerating the catalyst with a gas stream containing either nitrogen, oxygen, hydrogen, carbon monoxide or carbon dioxide gas.

U.S. Pat. No. 7,629,287 and WO0141926 relates to regeneration of hydro-oxidation catalyst such as gold, silver, platinum, lanthanide group metal incorporated onto titanium support. Regeneration is carried out using ozone gas at a temperature of 160° C.

U.S. Pat. No. 6,288,248 disclose a process for epichlorohydrin using allylchloride and hydrogen peroxide. U.S. Pat. No. 6,288,248 teaches the process of isolating the deactivated catalyst and regenerating the catalyst using methods in prior art such as washing techniques, high temperature calcinations and gas treatment at higher temperature, to improve the activity of the catalyst. However the overall process is time consuming as well as energy consuming.

Deactivation and regeneration of titano silicate catalyst during various processes such as propylene epoxidation, phenol hydroxylation, Cyclohexanone ammoximation, and oxidative cleavage of cyclohexene, by solvent washing and calcination are referred in journals Applied Catalysis A: General 307 (2006) 222; Catalysis Letters 97 No. 3-4, (2004) 233; J Mol Catal A: Chemical 273 (2007) 73; Applied Catalysis A: General 345 (2008) 195; Chemical Eng Journal 108 (2005) 187.

The method disclosed in these prior art for titanosilicate catalyst regeneration are time consuming as well as energy consuming and requires sophisticated reactor design and hardware requirements suitable for heating the catalyst bed to such a high temperatures.

Accordingly, there is a need for developing an effective process for regeneration of titanosilcate catalysts.

OBJECTS OF THE PRESENT INVENTION

Main object of the present invention to provide an effective process for the regeneration of deactivated titanium silicate catalysts.

Another object of the present invention is to provide a process for the regeneration of deactivated titanium silicate catalysts in which the activity of the regenerated titanosilicate catalyst is not lost rapidly.

Yet another object of the present invention is to provide a process for regeneration of deactivated catalysts without isolating or filtering the deactivated catalyst from the reaction system.

Yet another object of the present invention is to provide a regeneration process which is performed at moderate temperature and pressure.

Still, another object of the present invention is to provide a commercial viable process for oxidation reaction employing titanium silicate catalyst such as allyl chloride epoxidation, phenol hydroxylation and cyclohexene ammoximation.

SUMMARY OF THE PRESENT INVENTION

In accordance with the present invention, a process for activating a deactivated titano silicate catalyst, in a reactor, said process comprising the steps of;
i) washing the catalyst bed containing deactivated titano silicate at a temperature range of 20 to 40° C., with a solvent selected from the group consisting of alcohol, ester, ketone, water and aqueous hydrogen peroxide;
ii) heating the reactor to a temperature in the range of 50° C. to 100° C., to provide a heated catalyst bed;
iii) reacting the heated catalyst in the catalyst bed, with ozone gas under exothermic conditions, said reaction being carried out by feeding a gaseous mixture containing air/oxygen and ozone having ozone content in the range of 2 to 10%, and monitoring the outlet stream of the gas coming out through said bed for ozone seepage, said reaction continued till the ozone content in the outlet stream is at least 0.2%, to provide a regenerated catalyst; and iv) cooling the regenerated catalyst bed first by passing of air/oxygen gas through the said bed followed by washing of the said bed with a solvent selected from the group consisting of alcohol and water, to a temperature in the range of 20 to 40° C.

Typically, the steps (ii) and (iii) are repeated at least once, after cooling of the regenerated catalyst bed by air/oxygen gas in step (iv).

Typically, the temperature of the heated catalyst bed in the step (ii) is 80° C.

Typically, the solvent used in step (i) is an alcohol selected from the group consisting of methanol, ethanol, 1-propanol, 2-propanol, 2-methyl-2-propanol, 1-butanol, 2-butanol, and ethylene glycol.

Another aspect of the present invention is to provide an integrated process for the production of an oxidized product in an oxidation reaction employing titano silicate catalyst and hydrogen peroxide, said process being carried out in a reactor containing titano silicate catalyst bed and comprising the steps of:

A) performing oxidation reaction selected from the group consisting of allyl chloride epoxidation, phenol hydroxylation and cyclohexene ammoximation, in presence of hydrogen peroxide, to obtain an oxidized product;

B) monitoring the level of catalyst deactivation during the said oxidation reaction;

C) stopping the said reaction of step (A), when the level of catalyst deactivation in step B) shows catalyst weight loss of 8%;

D) activating the deactivated catalyst of step (C) in accordance with the process of claim 1, to obtain a regenerated catalyst;

E) resuming the said oxidation reaction of step (A) in presence of the regenerated catalyst of step (D), to provide an oxidized product.

Typically, the reactor is selected from the group consisting fixed bed reactor or tubular reactor.

A preferred embodiment of the present invention provides a process for allylchloride epoxidation reaction.

Typically, the step (A) of performing the allylchloride epoxidation reaction includes passing the reactants allylchloride, hydrogen peroxide and methanol through the catalyst bed containing titano silicate to obtain epichlorohydrin as an oxidized product.

Typically, the step (C) of stopping the reaction includes stopping the flow of reactants through the catalyst bed.

Typically, the step (E) of resuming the reaction includes passing the reactants through the catalyst bed containing regenerated catalyst.

Another aspect of the present invention is to provide a process for the phenol hydroxylation reaction.

BRIEF DESCRIPTION OF DRAWING

FIG. 1 illustrates Reactor set-up for Ozone treatment at 300 g scale

DETAILED DESCRIPTION OF THE INVENTION

Epichlorohydrin, is a valuable raw material for the manufacture of epoxy resins and various glycerol and glycidol derivatives such as plasticisers, stabilisers, elastomers, solvents, dyestuff intermediates, surface active agents and pharmaceuticals, as a cross-linking agent in modified starch and as intermediates for further synthesis. Epichlorohydrin is prepared by allylchloride epoxidation route.

A typical process for allyl chloride epoxidation is given below.

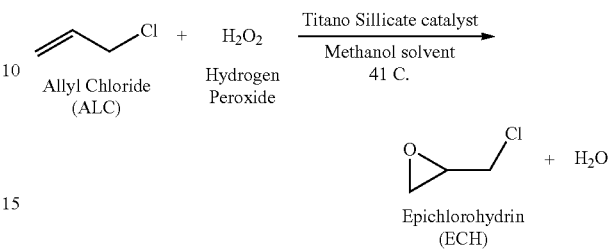

The process involves a reaction between Allyl chloride and hydrogen peroxide in the presence of titanosilcate catalyst.

The process is a continuous process and is carried out in a fixed bed or tubular reactor. The liquid feed containing allyl chloride, hydrogen peroxide, methanol and water is passed in an up-flow direction through the catalyst bed containing titanosilicate at a temperature range of 30 to 45° C. The oxidized product (epichlorohydrin) is collected from the top outlet.

The allyl chloride is 1-chloropropane and/or 2-chloropropane. Hydrogen peroxide is used as aqueous solution with content of hydrogen peroxide in the range from 10 to 90% by weight. Methanol acts a solvent.

The process is monitored periodically by checking the hydrogen peroxide concentration in the outlet stream. During the process, $H_2O_2$ content in the outlet stream is normally below 0.1% and the yield of Epichlorohydrin is found to be 98% based on hydrogen peroxide fed. The process is stopped when the hydrogen peroxide concentration in the outlet stream increases to 0.2% and above with subsequent decrease in the yield of epichlorohydrin. This decrease in the yield of the oxidized product is due to deactivation of the catalyst caused by organic deposition on the catalyst during the reaction. The level of deactivated catalyst is determined by thermogravimetric analysis (TGA). The TGA analysis of deactivated catalyst shows catalyst weight loss of around 8%. TGA analysis of fresh un-used catalyst is ~1% and this catalyst is highly active for epoxidation.

The present invention provides a method for regenerating the deactivated catalyst The process steps are as follows:

i. washing the catalyst bed containing deactivated titano silicate at a temperature range of 20 to 40° C., with a solvent selected from the group consisting of alcohol, ester, ketone, water and aqueous hydrogen peroxide.

ii. heating the reactor to a temperature in the range of 50 to 100° C.

iii. reacting the heated catalyst in the catalyst bed with ozone gas under exothermic conditions, by feeding a gaseous mixture containing air/oxygen and ozone gas having ozone content in the range of 2 to 10%, and monitoring the outlet stream of the gas coming out through the catalyst bed for ozone seepage. The reaction is continued till the ozone content in the outlet stream is at least 0.2%, to obtain regenerated catalyst.

iv. cooling the regenerated catalyst bed to a temperature in the range of 20 to 40° C., first by passing of air/oxygen gas through the bed followed by washing of the regenerated bed with a solvent.

Washing the catalyst bed with a solvent helps to remove most of the organic deposit on the catalyst bed. Most preferred solvent is an alcohol selected from the group consisting of lower aliphatic alcohols C1-C8 alcohols such as methanol, ethanol, isopropanol and butanol. Lower esters or low boiling ketones are also used as solvent. Preferably washing is carried out with methanol.

Optionally, after washing the deactivated catalyst bed with the above solvent, the catalyst bed may be further washed with an aqueous hydrogen peroxide solution to enable complete removal of the reactant i.e allyl chloride. The washed catalyst bed is then heated in presence of oxygen or oxygen enriched air to a temperature in the range of 50 to 100° C. When the temperature is in the range of 70 to 90° C., the external heating is stopped and a gaseous mixture containing ozone and air/oxygen is passed through the catalyst bed in an up flow direction. Ozone is provided from the ozone generator. Ozone generator is fitted in the air/oxygen line and the generator is adjusted in such a way the ozone is generated at the rate of 4-8 g/h and is mixed with 3-2 lit/min of air/oxygen. The content of ozone in the gaseous mixture is adjusted between 2 to 10%.

Exothermic reaction is observed initially at the bottom part of the reactor within minutes after starting the ozone treatment. The temperature increases from 80° C. to up to 300° C., after attaining the maximum temperature, the temperature at the bottom thermocouple decreases and that of the next level increases. A gradual increase in the temperature through different zones of the catalyst bed is observed indicating gradual ozone reaction along the flow of gas from bottom to the top of the catalyst bed. The outlet gas from the catalyst bed is found to be acidic with a pH of ~2 for certain period of operation. The outlet stream of the gases is checked for ozone seepage. During the process of activation, the outlet stream contains $CO_2$ and HCl vapors along with the oxygen, the ozone content in the outlet stream is nil, indicating complete usage of ozone in the reaction. When the ozone content in the outlet stream reaches to 0.2%, the process of activation is stopped. Increase in the ozone content in outlet stream indicates almost complete activation of the deactivated catalyst TG analysis of the regenerated catalyst showed that 75-85% of the organic heavies on the catalyst were decomposed during the 3-5 hr regeneration. TGA shows the catalyst weight loss between 180-650° C.~1-2%. This catalyst is again fit for epoxidation but gives little less on-time activity (before $H_2O_2$ seepage crosses 0.2%) compared to calcined catalyst. However, the difference is negligible compared to the ease of ozone assisted regeneration (in-situ, less temp, quick and less laborious) compared to calcinations. After the above ozone treatment, if the TGA analysis of the regenerated catalyst is high, more than 4%, then the catalyst bed is heated to 80° C. and the ozone treatment on the catalyst is repeated till the desired activity of the catalyst i.e TGA value of 1-2% is obtained.

The regenerated catalyst bed is then cooled to a temperature range of 20 to 40° C. with passing of air/oxygen through the catalyst bed. The regenerated catalyst is washed with a solvent containing mixture of methanol and water. The epoxidation reaction is then resumed by passing the reactants in the up flow direction through the regenerated catalyst bed. Similar seepage of hydrogen peroxide of below 0.1% is observed with regenerated catalyst.

The uniqueness of the process provided in accordance with the present invention lies in the fact that the regeneration of the catalyst is carried out in the same fixed bed or tubular reactor, and at a moderate temperature. Thus, the process eliminates repeated removal of the catalyst from the reactor.

Also, the external heat supplied for catalyst regeneration is sufficient to attain a temperature of ~100° C. which is much less compared to 400-600° C. as practiced in the prior art thereby making the regeneration process cost effective, less time consuming and energy saving.

The process of regeneration of the titanosilicate catalyst was also found to be effective for other oxidation process such as phenol hydroxylation and cyclohexene ammoximation.

The invention will now be described with respect to the following examples which do not limit the invention in any way and only exemplify the invention.

Example 1

Epoxidation of Allyl Chloride to Epichlorohydrin 270 g of titanosilicate (TS1) catalyst was taken in a 1 m SS tube reactor of 1 inch diameter. Catalyst bed was washed with methanol for 1 hr at a flow rate of 300 g/hr. Liquid feed of 36% Methanol, 3.5% $H_2O_2$, 3.5% $H_2O$ and 57% Allyl chloride was passed through the catalyst bed in up-flow direction at a flow rate of 680 g/hr. The cooling water flow from the reactor jacket was adjusted in such a way that the temperature of the liquid at the reactor outlet was maintained at 42° C. The outlet liquid was periodically sampled and analyzed for GC composition and hydrogen peroxide percentage (by titration). The $H_2O_2$ concentration in the outlet sample was found to be below 0.1% during the first 232 hrs of continuous run and the GC composition of the samples in this period showed 97.4% yield (on an average) of epichlorohydrin (ECH) based on $H_2O_2$ fed. On the 9th day, the $H_2O_2$ in the outlet stream was found to cross 0.1%, the epoxidation run was stopped and 0.2 g catalyst samples were taken out from 5 different sections of the reactor. The samples were analyzed by Thermogravimetric (TGA) technique. The catalyst showed an average weight loss of 6.15% between the temperature ranges of 180-650° C. in TGA. The catalyst was reloaded in the reactor for further epoxidation under similar conditions. It was found that after 52 hours of run the $H_2O_2$ seepage at the outlet crossed 0.2% mark and at this point the ECH yield, based on $H_2O_2$ fed, was found to drop to 93.1%. The epoxidation run was stopped, the samples were taken out again and analyzed in a similar manner as mentioned above. This time, the average weight loss of 8.6%, between the temperature ranges of 180-650° C., was observed in TGA. This TS1 catalyst was considered as a deactivated TS1 catalyst.

Comparative Example 1

Thermal Regeneration of the Deactivated TS1 Catalyst by Calcination/Thermal Treatment at 550° C.

The catalyst deactivated in Example 1 was taken in a Muffle Furnace and heated to 100° C. at the rate of 1° C./min and maintained 100° C. for 1 hr, temperature was further increased to 200° C. by heating at a rate of 5° C./min and maintained for 30 min, the temperature was gradually increased to 550° C. at a rate of 5° C./min and maintained for 5 hours. The catalyst was then allowed to attain the ambient temperature and samples were analyzed for TGA in a similar manner as mentioned in comparative example 1. The average weight loss of 0.92%, between the temperature ranges of 180-650° C., was observed in TGA.

Comparative Example 2

Epoxidation of Allyl Chloride to Epichlorohydrin with Thermal Regeneration Catalyst of Comparative Example 2

265 g of the catalyst regenerated in Comparative Example No. 1 was used for allyl chloride epoxidation to epichlorohydin in a similar manner as mentioned in Example 1. $H_2O_2$ seepage was found to cross 0.2% mark after 275 hours and the ECH yield at this point was 93.4%.

The TGA weight loss (between 180-650° C.) of 0.92% as in comparative example 1 is taken as a reference parameter for regeneration efficiency.

Example 2

Regeneration of the Deactivated TS1 Catalyst Using Ozone Treatment (Mixture of Ozone and Air)

Epoxidation run of allyl chloride to epichlorohydrin as mentioned in Example 1 was conducted for 276 hours (time when the $H_2O_2$ seepage crossed the 0.2% mark) and the catalyst samples showed average TGA weight loss (between 180-650° C.) of 8.55%.

20 g of this deactivated TS1 catalyst was taken in a SS 316 tube of 13 mm dia and 140 mm height. A thermocouple was inserted in the top portion of the catalyst bed. The SS tube was heated to the temperature of 80° C. in the presence of an air flow of 5 lit/min. On attaining the temperature, external heating was switched off and a gaseous mixture containing 1.5% ozone in 5 lit/min air flow was passed through the catalyst bed. Within few minutes of ozone passing over the catalyst bed, the temperature of the catalyst bed was found to increase due to heat generated by ozone treatment. This exotherm continued for some time and the temperature started decreasing again after attaining a maximum temperature of 98° C. The outlet gases from the catalyst bed were found to be acidic with a pH of ~2 for certain period of operation. The ozone content in the outlet gases was found to be nil initially for 2 hrs of the treatment. When the ozone content in the outlet gases increased to 0.1%, the heating and ozone generator was stopped, the catalyst showed TGA weight loss of 4.08%.

Example 3

Regeneration of the Deactivated TS1 Catalyst Using Ozone Treatment (Mixture of Ozone and Oxygen)

20 g of deactivated catalyst obtained during the epoxidation run of Example 2 was treated in similar manner as mentioned in the regeneration method of example 2 using oxygen instead of air, with a flow rate of 3 lit/min. The ozone concentration in the feed stream was found to be 2%. The catalyst bed temperature increased to 240° C. within 15 minutes (exotherm) of starting the treatment. The outlet gases were found to be more than 0.1% ozone after 45 minutes of the treatment. The ozone treatment was stopped after 45 minutes. The catalyst showed TGA weight loss of 3.31%.

The catalyst bed was cooled to 50-60° C. with an air flow of 5 lit/min and then heated again to a temperature of 80° C. in the presence of air. On attaining the temperature, external heating was switched off and a gaseous mixture containing 1.5% ozone in 5 lit/min oxygen flow was passed through the catalyst bed. Within few minutes of ozone passing over the catalyst bed, the temperature of the catalyst bed was found to increase due to heat generated because of ozone treatment. This exotherm continued for some time and the temperature started decreasing again after attaining a maximum temperature of 98° C. The outlet gases from the catalyst bed were found to be acidic with a pH of ~2 for certain period of operation. The ozone content in the outlet gases was found to be nil initially for 2 hrs of the treatment. When the ozone content in the outlet gases increased to 0.3%, the heating and ozone generator was stopped, the catalyst showed TGA weight loss of 1.9%.

Examples 4-10

Regeneration of the Deactivated TS1 Catalyst Using Ozone Treatment at Different Conditions In this set of examples, 20 g of deactivated catalyst obtained during the epoxidation run of Example 2 was treated in a similar manner as explained in Example 3 under different conditions. The treatment conditions and the result in the form of TGA weight loss are mentioned in the following table I.

| Expt. No. | Temperature ° C. | $O_3$ feed concentration % | $O_2$ flow rate lit/min | Gas Treatment Time Hours | TGA weight loss (Av.) % |
|---|---|---|---|---|---|
| 4 | 60 | 2 | 3 | 1 | 2.9 |
| 5 | 80 | 5 | 3 | 1 | 1.2 |
| 6 | 100 | 3 | 3 | 1 | 1.1 |
| 7 | 120 | 4 | 3 | 1 | 1.2 |
| 8 | 80 | 3 | 3 | 1 | 1.9 |
| 9 | 80 | 4 | 5 | 1 | 1.6 |
| 10 | 80 | 4 | 3 | 2 | 1.4 |

Examples 11

Regeneration of the Deactivated TS1 Catalyst Using Ozone at 270 gm Scale

Epoxidation reaction was carried out as mentioned in the Example 2 using 270 g of TS1 catalyst till the $H_2O_2$ seepage of 0.2%. At this stage, the liquid reactant stream was stopped and the deactivated catalyst was washed with 0.5 lit methanol methanol to get rid of un-reacted allyl chloride and reaction products, at the rate of 1 lit/hr rate. The residual methanol from the catalyst bed was drained out and the catalyst bed was heated to 80° C. for 10 minutes. Heating was switched off and ozone stream with 3% ozone in 3 lit/min oxygen was passed through the catalyst bed. The treatment was continued for 4 hours and the off-gases were monitored for Ozone seepage. It was observed that in the initial phase of treatment, there was no ozone coming out of the reactor indicating complete utilization of ozone. After 3.6 hours, the ozone concentration in the off-gases was found to be 0.5 g/hr, the ozone stream through the catalyst bed was stopped. The catalyst samples collected from different sections of the catalyst bed showed an average TGA weight loss of 1.8%.

Examples 12

Complete Cycle of Epoxidation—Regeneration with Ozone Treatment—Epoxidation Reactions at 270 gm Scale Epoxidation reaction was carried out as mentioned in the Example 2 using 270 g of TS1 catalyst till the $H_2O_2$ seepage of 0.2%. At this stage, the liquid reactant stream was stopped and the deactivated catalyst was washed with 0.5 lit methanol with a flow rate of 1 lit/hr to get rid of un-reacted allyl chloride and reaction products. The residual methanol from the catalyst bed was drained out and the catalyst bed was heated to 80° C. for 10 minutes. Heating was switched off and ozone stream with 3% ozone in 3 lit/min oxygen was passed through the catalyst bed. The treatment was continued for 4 hours, after which the ozone stream was put-off. The regenerated catalyst bed was washed first with water (600 g) followed by methanol (600 g) with a flow rate of 1 lit/hr. The residual methanol was drained out and the liquid feed stream of 36% Methanol, 3.5% $H_2O_2$, 3.5% $H_2O$ and 57% Allyl chloride was passed through the catalyst in up-flow direction at a flow rate of 680 g/hr. The epoxidation reaction was continued as explained in Example no. 1. The catalyst was found to give an activity for 268 hours before the $H_2O_2$ seepage crossing the 0.2% mark.

Examples 13

TS1 Catalyzed Phenol Hydroxylation and Regeneration Cycle 40 g of fresh TS 1 catalyst was taken in a tubular glass reactor of 1.25 cm dia and 40 cm height. The reactor was heated to 65° C. and a solution of 7.8% Phenol and 5.68% $H_2O_2$ in $H_2O$ was passed through the catalyst bed as an up-flow stream at the rate of 102 g/hr flow rate. The outlet stream was monitored for $H_2O_2$ seepage. The $H_2O_2$ seepage was found to increase gradually to 1.3% in 10 hrs. The catalyst was washed with water (100 g) and methanol (200 g) using the same flow-rates. The catalyst was dried by heating to 80° C. with 1 lit/min $O_2$ flow for 20 minutes, heating was stopped and ozone was passed through the bed at 2.5% concentration in 3 lit/min oxygen flow for 20 minutes. The catalyst temperature was found to rise to 145° C. in minutes after starting the ozone gas. After 4 hrs of ozone treatment, the catalyst was cooled, washed and reused for phenol hydroxylation reaction as mentioned above. Similar pattern of $H_2O_2$ seepage was again observed as above.

TECHNICAL ADVANCEMENT

The process for regeneration of the titanosilicate catalysts according to present invention offers several advancement over the prior art processes.

Heating of the catalyst at higher temperatures of 400-600° C. is not required;

Low temperature, in-situ catalyst regeneration is achieved;

The localized exotherm is achieved during the ozone—air treatment which gives effective regeneration without heating the whole lot of catalyst;

Cost-effective (in terms of reactor design, MOC (material of construction);

Energy saving (not much external heating/cooling is required);

Time saving as the regeneration is faster and cooling is also faster as there is very less bulk heating;

The numerical values of various parameters given in the specification are but approximations and slightly higher or slightly lower values of these parameters fall with in the ambit and the scope of the invention.

While considerable emphasis has been placed herein on the specific steps of the preferred process, it will be highly appreciated that many steps can be made and that many changes can be made in the preferred steps without departing from the principles of the invention. These and other changes in the preferred steps of the invention will be apparent to those skilled in the art from the disclosures herein, whereby it is to be distinctly understood that the foregoing descriptive matter is to be interpreted merely as illustrative of the invention and not as a limitation.

The invention claimed is:

1. A process for activating a deactivated titano silicate catalyst, in a reactor, said process comprising the following steps;
   i) washing the catalyst bed containing deactivated titano silicate at a temperature range of 20 to 40° C., with a solvent selected from the group consisting of alcohol, ester, ketone, water and aqueous hydrogen peroxide;
   ii) heating the reactor to a temperature in the range of 50° C. to 100° C., to provide a heated catalyst bed;
   iii) reacting the heated catalyst in the catalyst bed, with ozone gas under exothermic conditions, said reaction being carried out by feeding a gaseous mixture containing air/oxygen and ozone having ozone content in the range of 2 to 10%, and monitoring the outlet stream of the gas coming out through said bed for ozone seepage, said reaction continued till the ozone content in the outlet stream is at least 0.2%, to provide a regenerated catalyst; and
   iv) cooling the regenerated catalyst bed first by passing of air/oxygen gas through the said bed followed by washing of the said bed with a solvent selected from the group consisting of alcohol and water, to a temperature in the range of 20 to 40° C.

2. The process as claimed in claim 1, wherein the steps (ii) and (iii) are repeated at least once, after cooling of the regenerated catalyst bed by air/oxygen gas in step (iv).

3. The process as claimed in claim 1, wherein the temperature of the heated catalyst bed in the step (ii) is raised to 80° C.

4. The process as claimed in claim 1, wherein the solvent used in step (i) is an alcohol selected from the group consisting of methanol, ethanol, 1-propanol, 2-propanol, 2-methyl-2-propanol, 1-butanol, 2-butanol, and ethylene glycol.

5. The process as claimed in claim 1, wherein the gaseous mixture in the step (iii), is fed to the catalyst bed over a period of 2 to 6 hrs.

6. An integrated process for the production of an oxidized product in an oxidation reaction employing titano silicate catalyst and hydrogen peroxide, said process being carried out in a reactor containing titano silicate catalyst bed and comprising the following steps:
   A) performing oxidation reaction selected from the group consisting of allyl chloride epoxidation, phenol hydroxylation and cyclohexene ammoximation, in presence of hydrogen peroxide, to obtain an oxidized product;
   B) monitoring the level of catalyst deactivation during the said oxidation reaction;
   C) stopping the said reaction of step (A), when the level of catalyst deactivation in step B) shows catalyst weight loss of 8%;
   D) activating the deactivated catalyst of step (C) in accordance with the process of claim 1, to obtain a regenerated catalyst;
   E) resuming the said oxidation reaction of step (A) in the presence of regenerated catalyst of step (D), to provide an oxidized product.

7. The process as claimed in claim 1, wherein the reactor is selected from the group consisting of a fixed bed reactor and a tubular reactor.

8. The integrated process as claimed in claim 6, wherein the reactor is selected from the group consisting of a fixed bed reactor and a tubular reactor.

9. The integrated process as claimed in claim 6, wherein the oxidation reaction of step (A) is allylchloride epoxidation reaction.

10. The integrated process as claimed in claim 6, wherein the step (A) includes passing the reactants allylchloride, hydrogen peroxide and methanol through the catalyst bed containing titanosilicate to obtain epichlorohydrin as an oxidized product.

11. The integrated process as claimed in claim 6, wherein the step (C) of stopping the reaction includes stopping the flow of reactants through the catalyst bed.

12. The integrated process as claimed in claim 6, wherein the step (E) of resuming the reaction includes passing the reactants through the catalyst bed containing regenerated catalyst.

13. The integrated process as claimed in claim 6, wherein the oxidation reaction of step (A) is phenol hydroxylation reaction.

14. The integrated process as claimed in claim 6, wherein the oxidized product is an oxidized form of phenol.

\* \* \* \* \*

UNITED STATES PATENT AND TRADEMARK OFFICE
CERTIFICATE OF CORRECTION

PATENT NO. : 8,679,999 B2
APPLICATION NO. : 13/755689
DATED : March 25, 2014
INVENTOR(S) : Subbareddy Kanagasabapathy et al.

It is certified that error appears in the above-identified patent and that said Letters Patent is hereby corrected as shown below:

Title Page, item [75] should read as follows
Inventors: Yogesh Laxman BOROLE and Arati VARMA Signed and Sealed this
Eighth Day of July, 2014

Michelle K. Lee
*Deputy Director of the United States Patent and Trademark Office*

UNITED STATES PATENT AND TRADEMARK OFFICE
CERTIFICATE OF CORRECTION

PATENT NO.        : 8,679,999 B2
APPLICATION NO.   : 13/755689
DATED             : March 25, 2014
INVENTOR(S)       : Subbareddy Kanagasabapathy et al.

Page 1 of 1

It is certified that error appears in the above-identified patent and that said Letters Patent is hereby corrected as shown below:

Title Page, item [75] second and fourth inventor names should read as follows
Inventors: Yogesh Laxman BOROLE and Arati VARMA This certificate supersedes the Certificate of Correction issued July 8, 2014.

Signed and Sealed this
Fifth Day of August, 2014

Michelle K. Lee
*Deputy Director of the United States Patent and Trademark Office*